United States Patent [19]

Wettling

[11] Patent Number: 5,792,884
[45] Date of Patent: Aug. 11, 1998

[54] PREPARATION OF TERTIARY PHOSPHINES

[75] Inventor: Thomas Wettling, Limburgerhof, Germany

[73] Assignee: BASF Aktiengesellschaft, Ludwigshafen, Germany

[21] Appl. No.: 170,985

[22] Filed: Dec. 21, 1993

Related U.S. Application Data

[63] Continuation of Ser. No. 996,311, Dec. 23, 1992, abandoned.

[30] Foreign Application Priority Data

Dec. 23, 1991 [DE] Germany .............. 41 42 679.1

[51] Int. Cl.$^6$ .............................................. C07F 9/02
[52] U.S. Cl. .............................................. 568/17; 568/8
[58] Field of Search .............................................. 568/17, 8

[56] References Cited

U.S. PATENT DOCUMENTS 3,405,180  10/1968  Natoli et al. .
3,481,988  12/1969  Wunsch et al. .................. 260/606.5
3,780,111  12/1973  Young et al. .
4,008,282  2/1977  Townsend et al. .................. 260/606.5
4,036,889  7/1977  Chopdecker et al. .
4,131,624  12/1978  Davis et al. .................. 260/606.5

FOREIGN PATENT DOCUMENTS 12 47 310  8/1967  Germany .
24 55 371  6/1975  Germany .
26 38 720  1/1979  Germany .
28 28 604  1/1979  Germany .
1 259 883  2/1988  Germany .

*Primary Examiner*—Alan Siegel
*Attorney, Agent, or Firm*—Keil & Weinkauf

[57] ABSTRACT

Tertiary phosphines (I) are prepared by reducing the corresponding phosphine oxides (IIa) or phosphine dihalides (IIb) using silicon or a silicon alloy as reducing agent.

2 Claims, No Drawings

PREPARATION OF TERTIARY PHOSPHINES

This application is a continuation of application Ser. No. 07/996,311, filed on Dec. 23, 1992, now abandoned.

The present invention relates to an improved process for preparing tertiary phosphines (I) by reduction of the corresponding phosphine oxides (IIa) or phosphine dihalides (IIb).

Tertiary phosphines such as triphenylphosphine and tributylphosphine are important agents for organic syntheses by the Wittig method for preparing olefinic compounds. For example, they are of great importance for the industrial production of vitamin A.

In these syntheses, the tertiary phosphines are converted into the corresponding phosphine oxides for which there are relatively few direct applications. It has therefore long been the aim to convert phosphine oxides to tertiary phosphines by reacting them with reducing agents such as alanates, boranates, trimethylchlorosilane and systems such as triethyloxonium tetrafluoroboranate/magnesium, active carbon/white oil or hydrogen/silicon tetrachloride or by initially converting them into the corresponding phosphine dihalides and then reducing the latter with sodium (DE-A 26 38 720), iron (U.S. Pat. No. 3,780,111) or aluminum (DE-C 12 59 883).

However, none of these processes has become established in industry for various reasons, eg. because some of the reducing agents are too costly, the yields and selectivities are unsatisfactory and the resulting mixtures involve considerable technical problems in separating the solids. Also disadvantageous are highly corrosive gases such as hydrogen chloride and bromide which are produced in the reduction of phosphine dihalides with hydrogen (JP-A 55/149 294).

It is an object of the present invention to regenerate tertiary phosphines in a more economic and technically simpler manner than hitherto from the corresponding phosphine oxides or phosphine dihalides.

We have found that this object is achieved by a process for preparing tertiary phosphines (I) by reduction of the corresponding phosphine oxides (IIa) or phosphine dihalides (IIb), wherein silicon or a silicon alloy is used as reducing agent.

Particularly suitable starting compounds are phosphine oxides of the formula IIa'

$$R_3P=O \qquad \text{IIa'}$$

where the R radicals can be identical or different and are $C_1$–$C_{20}$-alkyl, $C_5$–$C_{12}$-cycloalkyl, aralkyl or aryl, it also being possible for two R radicals to form a 4- to 8-membered ring with the phosphorus atom.

The same applies to the phosphine dihalides of the formula IIb'

where X is chlorine or bromine, preferably chlorine.

The R radicals can also carry one or more inert substituents, for example halogen, alkyl or alkoxy.

In general, findings to date indicate that the process according to the invention takes place satisfactorily irrespective of the nature of R.

In principle, the phosphine oxides IIa can be reduced directly

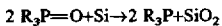

$$2\,R_3P=O + Si \to 2\,R_3P + SiO_2$$

but the phosphine dihalides IIb are preferred because they result not in the solid silicon dioxide but in the liquid silicon tetrahalides which can be separated from the phosphines I particularly straightforwardly by distillation.

Examples of industrially important phosphine dihalides IIb are the chlorides and bromides of the following tertiary phosphines:

tripropylphosphine
tributylphosphine
tricyclohexylphosphine
tricyclododecylphosphine
triphenylphosphine
tritolylphosphine
trianisylphosphine
trinaphthylphosphine
di(chlorophenyl)phenylphosphine and
dibutylphenylphosphine.

The phosphine dihalides IIb can be obtained in a conventional manner from the corresponding phosphines IIa, for example by reaction with phosphorus pertahalides, or in the case of the phosphine dichlorides by reaction with phosgene or thionyl chloride (DE-C 11 92 205 and Houben-Weyl, Methoden d. Org. Chemie, Vol. 12/1, p. 129 (1963)).

Silicon or a silicon alloy is used as reducing agent, preferably relatively pure silicon containing, for example, from 98 to more than 99.9% by weight of silicon or industrial crude silicon containing from about 90 to 98% by weight of silicon.

Also suitable are silicon alloys such as ferrosilicon which preferably contains more than 50% by weight of silicon, or silicon carbide.

Although by-products are formed when impure silicon or silicon alloys are used, they are in relatively small amounts so that workup of the reaction mixture is not greatly impeded.

Since the reaction is heterogeneous, it is beneficial for the reducing agent to be finely divided. It is therefore advisable to choose silicon or silicon alloys in the form of powders or granules with a median particle size of about 0.05–5 mm.

It is possible to employ the reducing agent in stoichiometric amounts, but it is advisable to use a small excess in order to increase the reaction rate. It is advantageous to use from 0.5 to 10, preferably from 0.8 to 5, mol of silicon per mol of phosphine oxide IIa or phosphine dihalide IIb. Unreacted silicon can be recovered and reused.

Used as reaction medium are organic liquids which are inert under the reaction conditions. It is advantageous to use polar, high-boiling aliphatic and aromatic hydrocarbons such as halohydrocarbons, chlorobenzene, o-dichlorobenzene and benzonitrile. Ethers and polyethers are also suitable. However, non-polar hydrocarbons can also be used. It is usually expedient to carry out the reaction in an amount of from 0.5 to 10 kg of liquid per kg of IIa or IIb.

The reaction can also be carried out without these liquid reaction media; thus they can be dispensed with when the starting materials IIa or IIb are liquid. When solid starting materials are reacted, it is advantageous to add a tertiary phosphine corresponding to the particular product of the process in order to depress the melting point of the starting materials and to carry out the reduction in this liquid reaction medium. In this case it is advisable to use an amount of from 0.1 to 1 kg of tertiary phosphine per kg of IIa or IIb.

The reduction is preferably carried out at from 100° to 300° C., in particular from 100° to 250° C. Below 50° C. the reaction rate is too slow and above 300° C. side reactions are likely to become noticeable.

The reaction takes place under a pressure from about 0.5 to 50 bar. The reaction is normally carried out under atmospheric pressure, but it is also possible to raise the pressure in order to increase the reaction rate.

The reaction can be carried out either batchwise or continuously. If the phosphine oxides IIa are used as starting materials, it is advisable for catalytic amounts of a halogenating agent, preferably silicon tetrachloride, to be present. It is advisable in the reaction of IIb to remove the silicon tetrahalide by-product continuously from the reaction mixture by distillation in order to increase the reaction rate. The reaction mixture is worked up by conventional methods such as distillation, extraction and recrystallization.

The advantage of the process according to the invention compared with the prior art, particularly when the phosphine dihalides are used as starting materials, is that the by-products are liquid silicon tetrahalides which can be straightforwardly removed from the reaction mixture by distillation, so that no elaborate working up of the reaction product is necessary. An additional advantage is that the silicon tetrahalide by-products can be used as starting material for preparing high-purity silicon and valuable organosilicon compounds.

The reduction process according to the invention is particularly important for preparing triphenylphosphine from triphenylphosphine oxide or triphenylphosphine dichloride.

EXAMPLE 1

Preparation of Triphenylphosphine from Triphenylphosphine Oxide 70 g (0.25 mol) of triphenylphosphine oxide were reacted with 7 g (0.25 mol) of silicon powder in 70 g of benzonitrile, 2 g (0.012 mol) of silicon tetrachloride and 0.5 g (0.003 mol) of iron trichloride in an autoclave at 190° C. for 48 hours.

Analysis of the reaction mixture by $^{31}$P-NMR spectroscopy showed the yield of triphenylphosphine to be 20%.

EXAMPLE 2

Preparation of Triphenylphosphine from Triphenylphosphine Dichloride 333 g (1 mol) of triphenylphosphine dichloride and 28 g (1 mol) of silicon powder were introduced into 150 ml of o-dichlorobenzene and heated to 165° C. The silicon tetrachloride produced during a reaction time of 1 hour was removed by distillation. The mixture was then heated to 170° C. and stirred at this temperature for 2 hours. Then the o-dichlorobenzene was removed by distillation, and unreacted silicon was separated from the crude product by filtration. Workup of the filtrate resulted in 99% yield of triphenylphosphine.

EXAMPLE 3

Preparation of Triphenylphosphine from Triphenylphosphine Dichloride 333 g (1 mol) of triphenylphosphine dichloride and 28 g (1 mol) of silicon powder were reacted in 150 ml of benzonitrile at 180° C. for 2 hours. The silicon tetrachloride produced in the reaction was continuously removed from the mixture by distillation.

The reaction mixture was worked up as in Example 2. The yield of triphenylphosphine was 99%.

EXAMPLE 4

Preparation of Triphenylphosphine from Triphenylphosphine Dichloride 333 g (1 mol) of triphenylphosphine dichloride and 14 g (0.5 mol) of silicon powder were reacted in 150 ml of benzonitrile at 180° C. for 4 hours.

The subsequent procedure was as in Example 2. The yield of triphenylphosphine was 98%.

EXAMPLE 5

Preparation of Triphenylphosphine from Triphenylphosphine Dichloride

Triphenylphosphine dichloride which had been prepared by reacting 139 g (0.5 mol) of triphenylphosphine oxide with 59 g (0.6 mol) of phosgene at 210° C. was cooled to 140° C., and 66 g (0.25 mol) of triphenylphosphine were added. 14 g (0.5 mol) of silicon powder were added and then the triphenylphosphine dichloride was reduced at 185° C. for 2 hours, removing the silicon tetrachloride by-product by distillation.

Analysis of the reaction mixture by $^{31}$P-NMR spectroscopy showed the yield of triphenylphosphine to be 90%.

I claim:

1. A process for preparing a tertiary phosphine which comprises: heating a phosphine dihalide in the presence of silicon powder at a temperature of from 100° to 300° C. to reduce the phosphine dihalide to the tertiary phosphine.

2. A process for preparing triphenyl phosphine which comprises: heating triphenylphosphine dichloride in the presence of silicon powder at a temperature of from 100° to 250° C. to reduce the triphenylphosphine, dichloride to triphenyl phosphine.

* * * * *

UNITED STATES PATENT AND TRADEMARK OFFICE
CERTIFICATE OF CORRECTION

PATENT NO.: 5,792,884

DATED: August 11, 1998

INVENTOR(S): Thomas WETTLING

It is certified that error appears in the above-identified patent and that said Letters Patent is hereby corrected as shown below:

Col. 4, claim 2, line 53, delete the comma ",".

Signed and Sealed this

Twenty-seventh Day of October, 1998

*Attest:*

BRUCE LEHMAN

*Attesting Officer*      *Commissioner of Patents and Trademarks*